United States Patent [19]

Suzuki

[11] 4,217,419

[45] Aug. 12, 1980

[54] DRIED LACTIC ACID BACTERIA COMPOSITION

[75] Inventor: Tadao Suzuki, Tokyo, Japan

[73] Assignee: Ajinomoto Company, Incorporated, Tokyo, Japan

[21] Appl. No.: 845,931

[22] Filed: Oct. 27, 1977

[30] Foreign Application Priority Data

Oct. 28, 1976 [JP] Japan .................................. 51-129843

[51] Int. Cl.² .......................... C12N 1/20; C12N 1/04; C12Q 1/29
[52] U.S. Cl. ..................................... 435/253; 435/29; 435/260
[58] Field of Search .................... 195/96, 59, 65, 100, 195/102, 99, 103.5 R; 426/61; 435/29, 260, 253

[56] References Cited

U.S. PATENT DOCUMENTS

| | | | |
|---|---|---|---|
| 3,080,236 | 3/1963 | Ferguson | 426/61 |
| 3,897,307 | 7/1975 | Porubcan et al. | 426/61 |
| 4,066,794 | 1/1978 | Schur | 426/61 |

OTHER PUBLICATIONS

Platt et al., "Microbiological Assays", *Handbook of Microbiology,* vol. 3, Laskin et al., ed. (1973), CRC Press, Inc., Cleveland, pp. 1017–1025.

Lapage et al., "Preservation of Microorganisms," *Handbook of Microbiology,* vol. I, Laskin et al., ed., (1973), CRC Press Inc., Cleveland, pp. 713–724.

*Primary Examiner*—Thomas G. Wiseman
*Attorney, Agent, or Firm*—Oblon, Fisher, Spivak, McClelland & Maier

[57] ABSTRACT

A dried lactic acid bacteria composition comprising lactic acid bacteria and alginate, which is effective for the preservation of said bacteria therein.

3 Claims, 35 Drawing Figures

DRIED LACTIC ACID BACTERIA COMPOSITION

BACKGROUND OF THE INVENTION

1. Field of the Invention

This invention relates to a dried lactic acid bacteria composition comprising lactic acid bacteria and alginate.

2. Description of the Prior Art

There are some methods available for the long-term preservation of lactic acid bacteria, including those which consist of cold storing the microbes covered with liquid paraffin after passage on maintenance media or of cold storing them after they have been suspended in dried skim milk and then lyophilized. In these methods, which are designed to preserve the microbes over a long period of time, the microbes are reanimated before use by being subjected to the process of passage on restoration media. Microbes used for microbioassay must be highly viable. Those preserved by conventional methods require various preparatory procedures which are too sophisticated and time-consuming to promptly serve the practical purpose.

SUMMARY OF THE INVENTION

Accordingly, it is an object of the present invention to provide a less complicated procedure of microbioassay. With this objective in mind the inventor made intensive studies to work out a method by which microbes can be used for this purpose as soon as they are needed. This invention was brought to completion with the finding that a dried microbial culture containing alginate can be left for a long time without significant loss of microbial activity because alginate is effective for preserving dried microbes.

BRIEF DESCRIPTION OF THE DRAWINGS

A more complete appreciation of the invention and many of the attendant advantages thereof will be readily attained as the same becomes better understood by reference to the following detailed description when considered in connection with the accompanying drawing, wherein.

DETAILED DESCRIPTION OF THE PREFERRED EMBODIMENTS

Figure 1A:
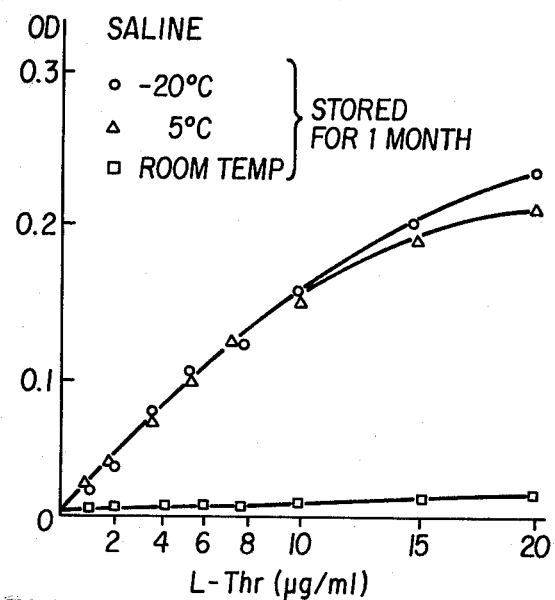
FIGS. 1, 2 and 3 show the results of the preservation test of Example 1.

The microbes covered by the invention are those used for the microbioassay of amino acids, vitamins and the like, including *Lactobacillus arabinosus* 17-5 ATCC 8014, *Lactobacillus casei* ATCC 7469, *Lactobacillus fermenti* 36 ATCC 9338, *Leuconostoc mesenteroides* P-60 ATCC 8042, *Leuconostoc citrovorum* ATCC 8081, *Streptococcus faecalis* R ATCC 8043, *Lactobacillus leichmannii* ATCC 4797 or ATCC 7830.

The alginate referred to in the context of this invention is represented by sodium alginate.

In a typical process for producing the composition of this invention, microbes may be dehydrated by any one of the generally known methods for drying them in aqueous solution, e.g., lyophilization of an alginate solution, in which microbes are suspended beforehand.

The dried microbe composition of the invention may be stored in ampoules, for example, where better preservation can be achieved because oxygen is absent. No cold storage is necessary for up to one month. Dry culture dissolved in saline, sterilized, distilled or purified water or medium for assay, each added after 6 months' cold storage of the culture proved to be of as satisfactory use in amino acid or vitamin assay as that preserved by conventional methods.

Some actual examples are illustrated below to present the invention in further detail.

EXAMPLE 1

One loopful of stock culture of Lactobacillus maintained by passage at 2 weeks' intervals was inoculated into the pre-incubation medium shown below and then incubated at 37° C. for 16 to 20 hours. The culture so incubated was centrifuged at 1,500 r.p.m. for 5 minutes and, after removal of the supernatant (medium) in an aseptic manner, suspended in 2-5 times the volume of sterilized saline and then centrifuged again. This washing step was repeated up to 3 times as required.

| Contents | Weight |
| --- | --- |
| Yeast extract | 0.6 g |
| Polypeptone | 1.0 g |
| Glucose | 1.0 g |
| Potassium acetate | 1.0 g |
| $K_2HPO_4$ | 25 mg |
| $KH_2PO_4$ | 25 mg |
| $MgSO_4 \cdot 7H_2O$ | 10 mg |
| $FeSO_4 \cdot 7H_2O$ | 0.5 mg |
| $MnSO_4 \cdot 4H_2O$ | 0.5 mg |
| NaCl | 0.5 mg |
| Distilled water | 100 ml |
| pH = 6.8 | |

After washing, the culture was suspended in sterilized saline, 5 percent glucose solution, 0.1 percent solution of sodium alginate and 1 percent casein solution so as to give an absorbance (OD) value of 0.6 for each solution. A definite volume of each of these suspensions was dispensed in ampoules, lyophilized, sealed and then stored at 5° C. or −20° C.

Ampoules containing the stock culture, stored in the refrigerator at −20° C., were then left at room temperature for 10 minutes or more and then unsealed before dissolving the contents in 10 times the volume of saline, distilled or purified water or medium for assay. One drop (0.05 ml) of each of the resulting solutions was inoculated into tubes containing the medium for assay and a standard amino acid solution. The tubes were then covered and incubated at 37° C. for 16–20 hours before measurement of absorbance (OD) at 615 nm with a lightpath of 5 mm.

Figure 1B:
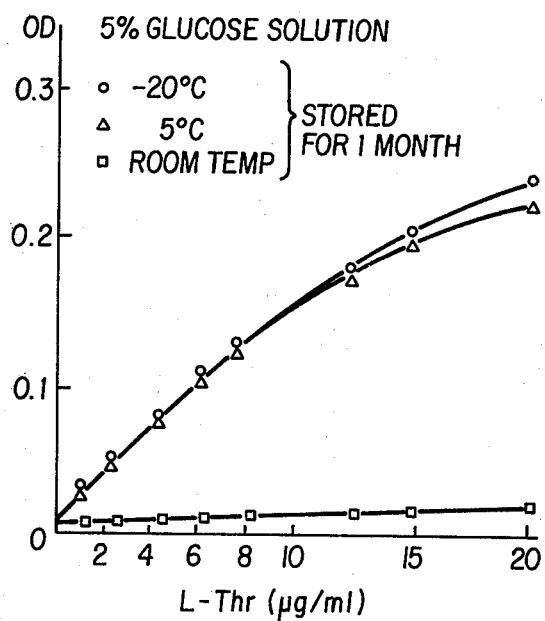
Figure 1C:
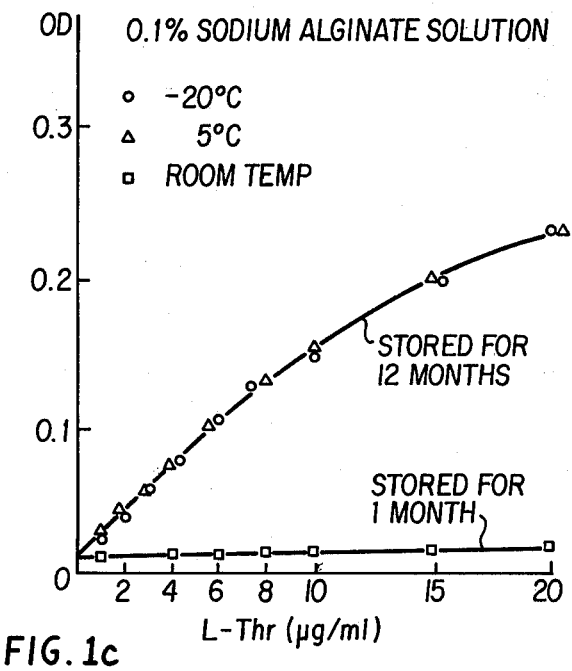
Figure 1D:
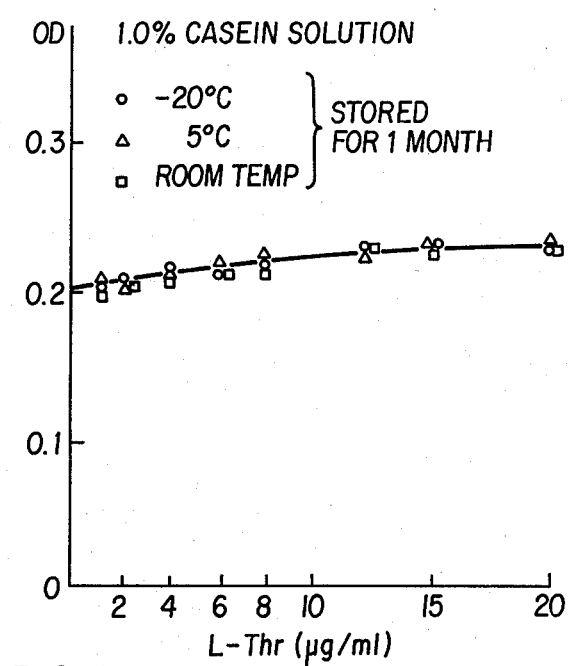
Figure 2A:
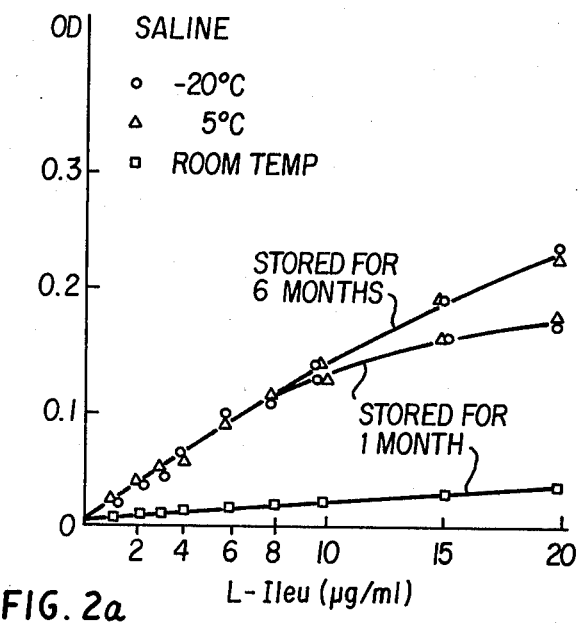
Figure 2B:
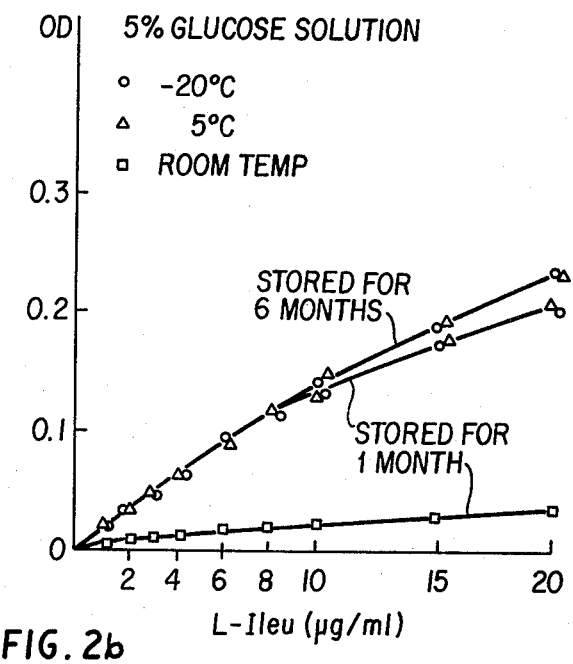
Figure 2C:
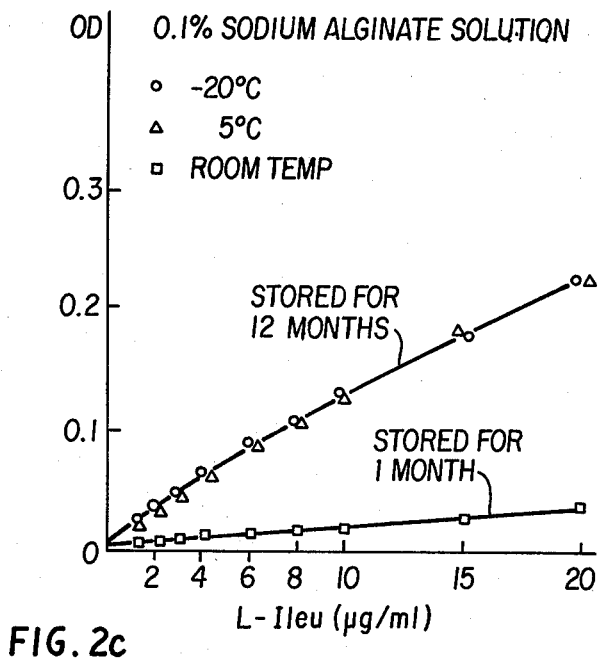
Figure 2D:
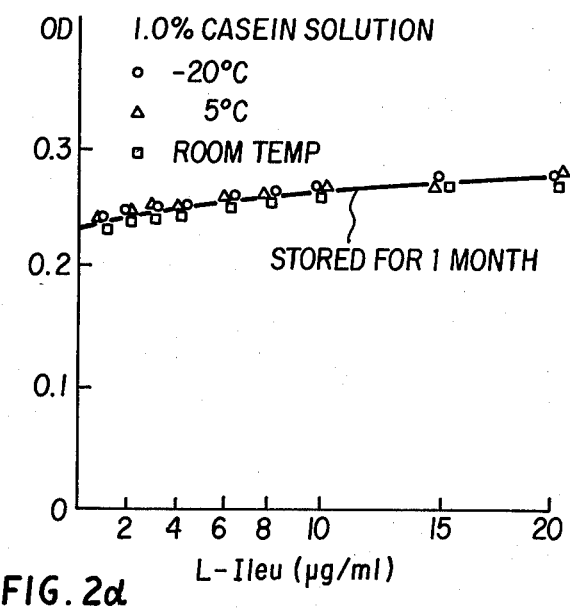
Figure 3A:
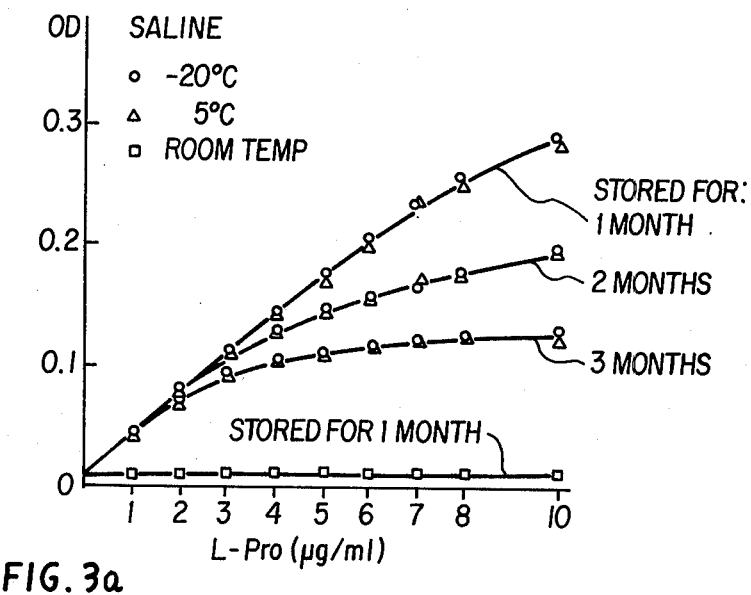
Figure 3B:
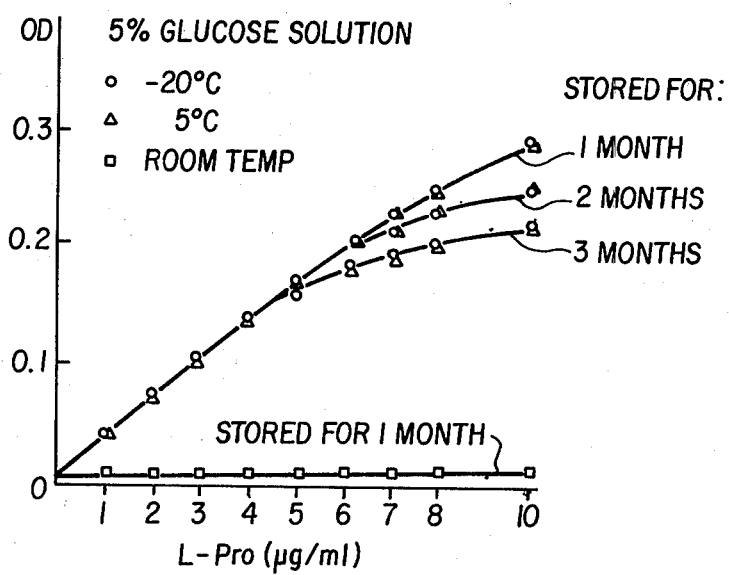
Figure 3C:
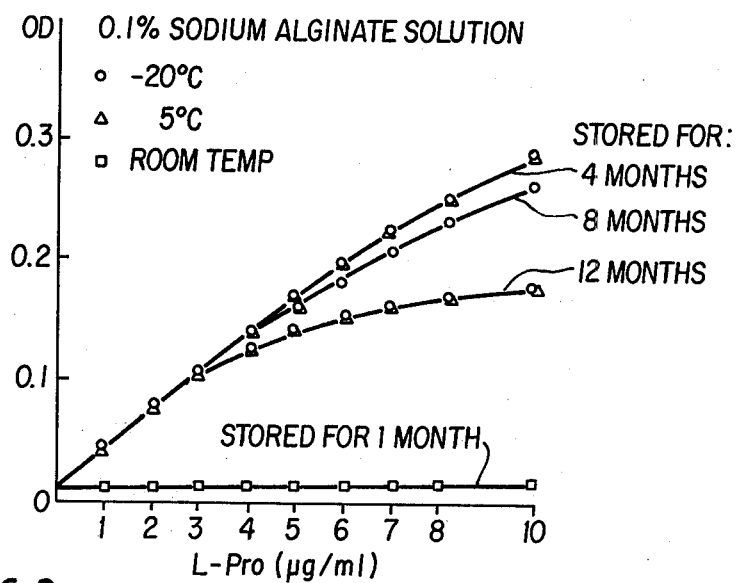
Figure 3D:
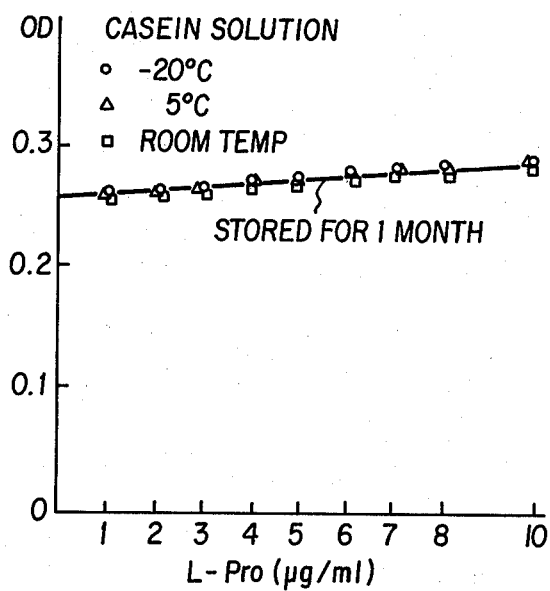

The results of preservation test of *Streptococcus faecalis* R ATCC 8043, *Leuconostoc mesenteroides* P-60 ATCC 8042 and *Leuconostoc citrovorum* ATCC 8081 are summarized in FIG. 1, 2 and 3.

EXAMPLE 2

Lyophilized stock culture of lactobacillus was prepared as described in Example 1. After storage at 5° C. for 12 months, the ampoules each containing an aliquot of the culture were unsealed in the same way as in Example 1. Each aliquot contained was then dissolved in 10 times the volume of culture for assay (or stock culture). The solution this obtained, together with an amino acid solution for standardization added in the same way as in Example 1, was incubated at 37° C. for 16–20 hours before measurement of absorbance (OD) at 615 nm and subsequent preparation of standard curves.

Figure 4:
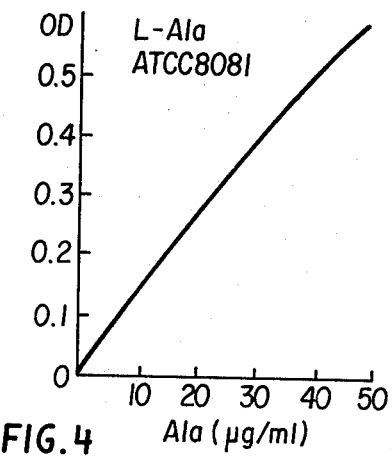
FIGS. 4-26 show the standard curves prepared in Example 2.
Figure 5:
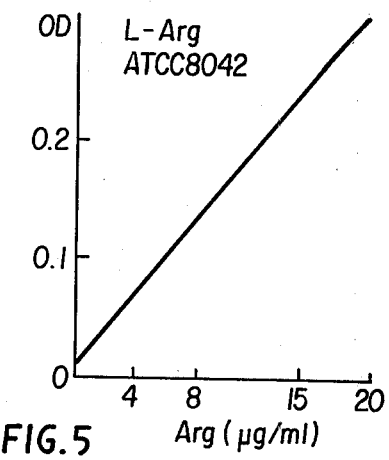
Figure 6:
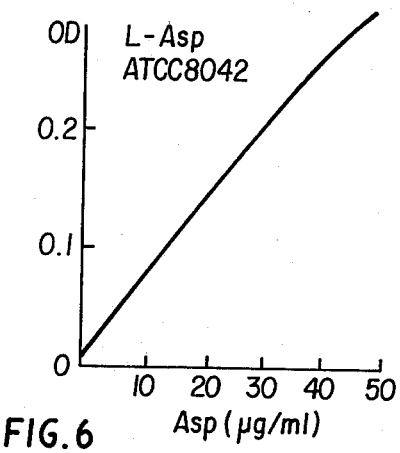
Figure 7:
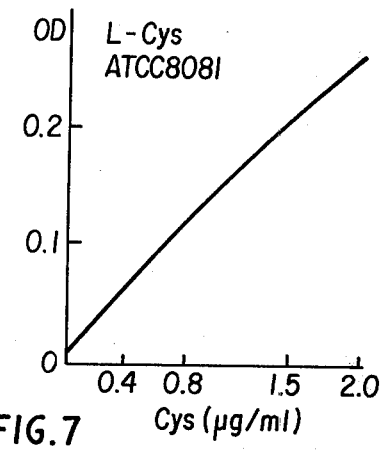
Figure 8:
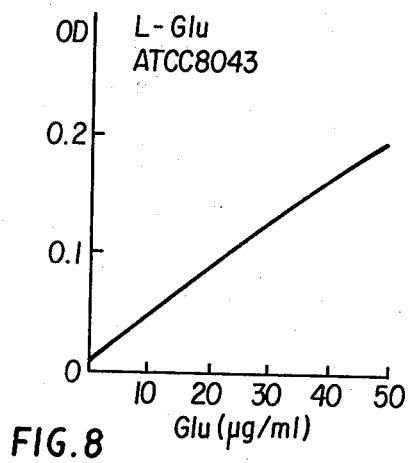
Figure 9:
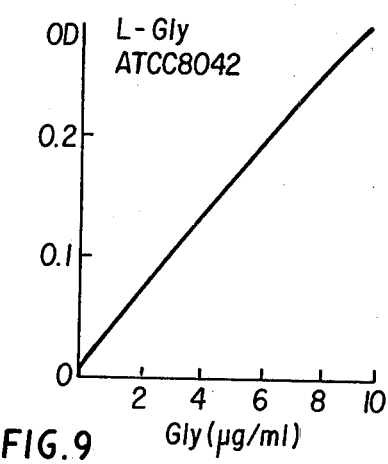
Figure 10:
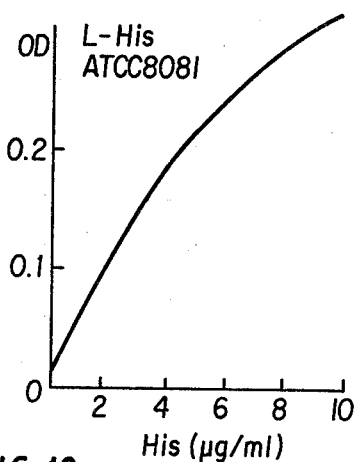
Figure 11:
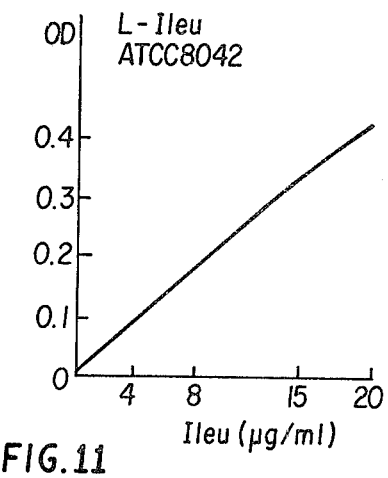
Figure 12:
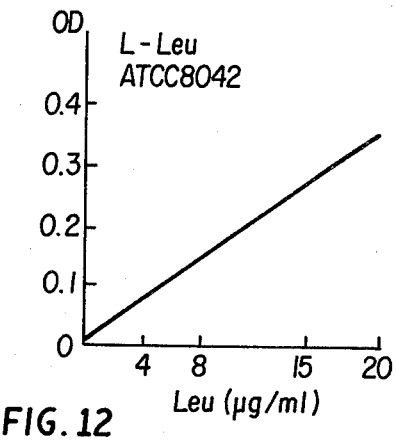
Figure 13:
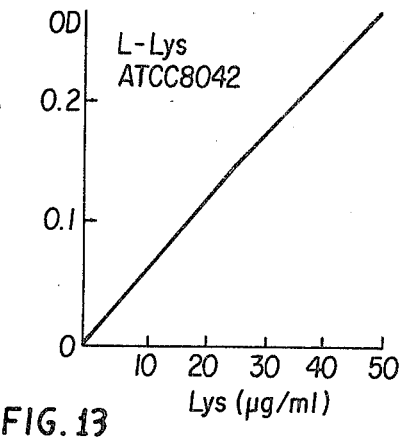
Figure 14:
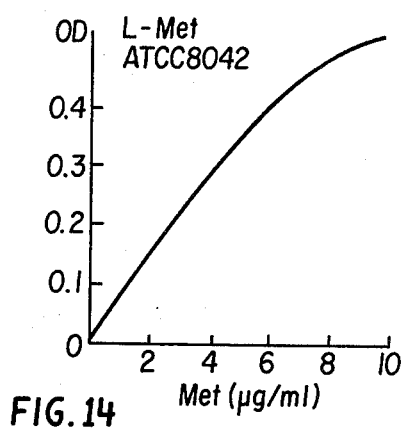
Figure 15:
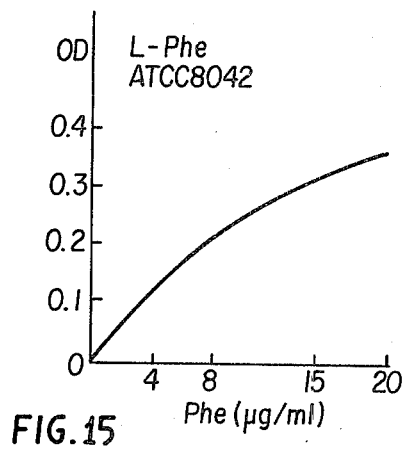
Figure 16:
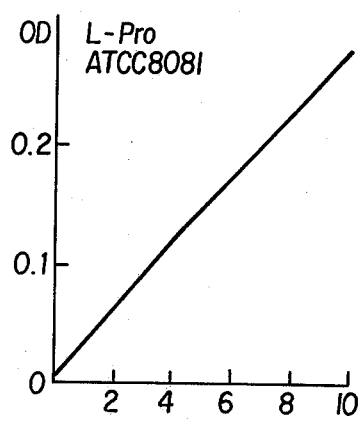
Figure 17:
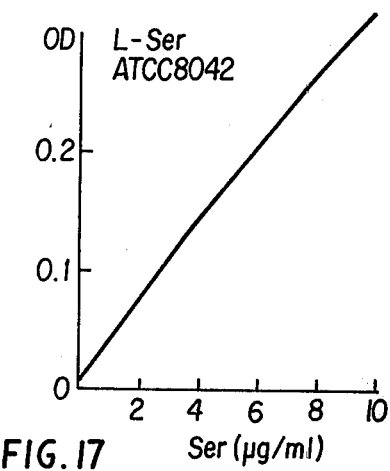
Figure 18:
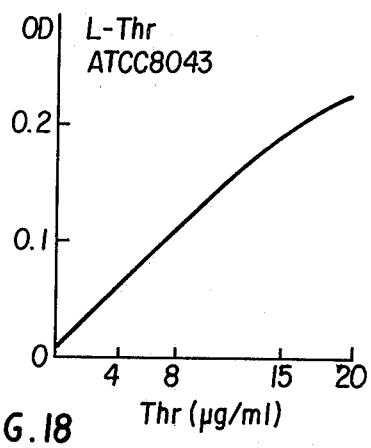
Figure 19:
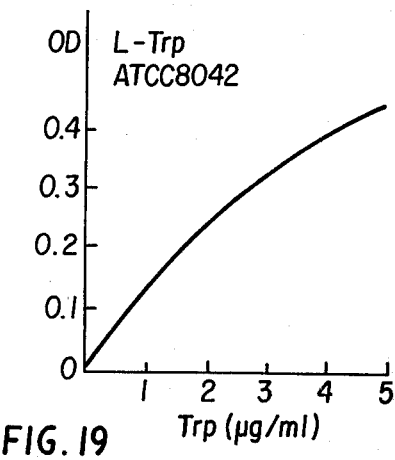
Figure 20:
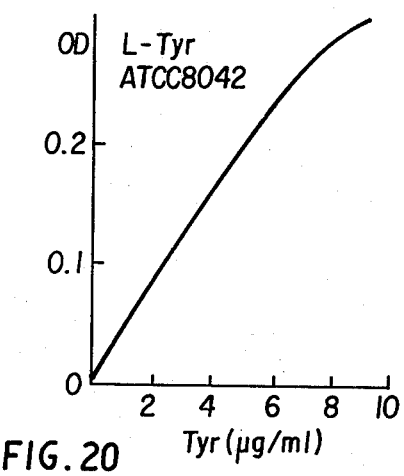
Figure 21:
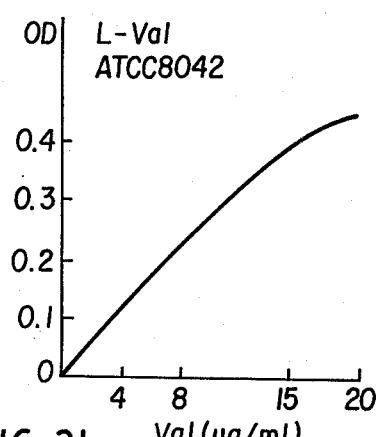
Figure 22:
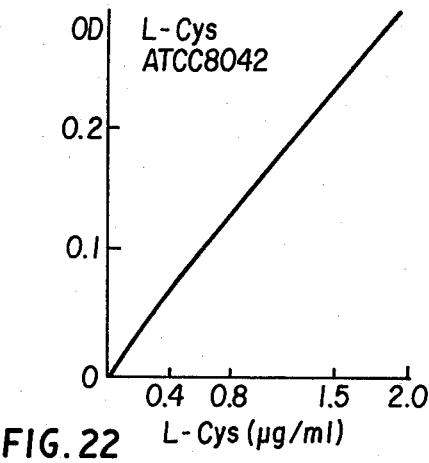
Figure 23:
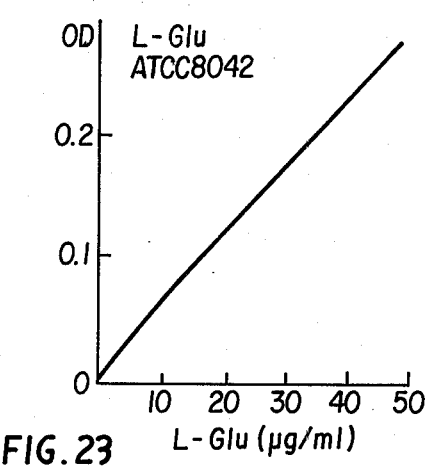
Figure 24:
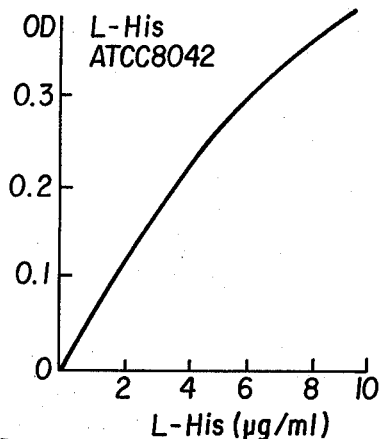
Figure 25:
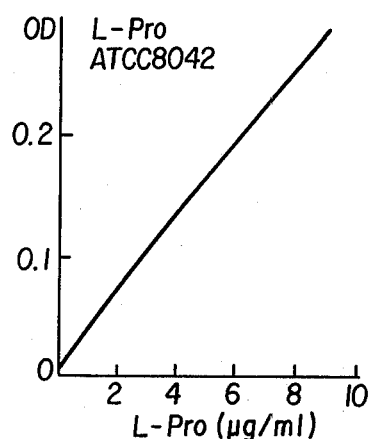
Figure 26:
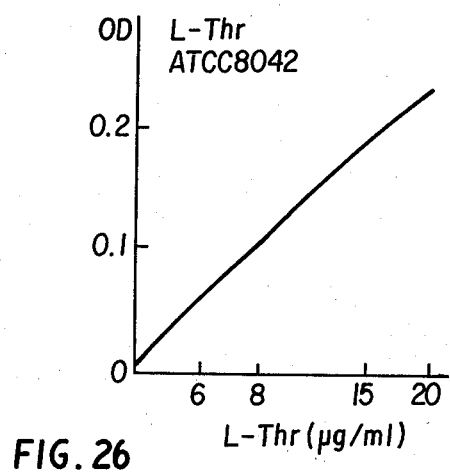

The results obtained are shown in FIG. 4 through FIG. 26.

What is claimed is:

1. A dried lactic acid bacteria compostion capable of being reconstituted to aqueous solution by the addition of water thereto consisting essentially of viable lactic acid bacteria and preserving amounts of sodium alginate prepared by forming a suspension of lactic acid bacteria in a solution containing sodium alginate in an amount effective for preserving said lactic acid bacteria, and dehydrating the resulting suspension.

2. The composition of claim 1 wherein said sodium alginate is added in an amount of 0.1% by weight.

3. A composition as set forth in claim 1 wherein said composition is in a freeze-dried form.